(12) United States Patent
Chene

(10) Patent No.: US 11,927,831 B2
(45) Date of Patent: Mar. 12, 2024

(54) METHOD FOR DETERMINING AT LEAST ONE GEOMETRICO-MORPHOLOGICAL PARAMETERS OF A SUBJECT IN A NATURAL POSTURE FOR DETERMINING A VISION CORRECTION EQUIPMENT

(71) Applicant: ESSILOR INTERNATIONAL, Charenton-le-Pont (FR)

(72) Inventor: Sylvain Chene, Charenton-le-Pont (FR)

(73) Assignee: Essilor International, Charenton-le-pont (FR)

( * ) Notice: Subject to any disclaimer, the term of this patent is extended or adjusted under 35 U.S.C. 154(b) by 284 days.

(21) Appl. No.: 17/279,973

(22) PCT Filed: Sep. 24, 2019

(86) PCT No.: PCT/EP2019/075742
§ 371 (c)(1),
(2) Date: Mar. 25, 2021

(87) PCT Pub. No.: WO2020/064755
PCT Pub. Date: Apr. 2, 2020

(65) Prior Publication Data
US 2022/0035182 A1    Feb. 3, 2022

(30) Foreign Application Priority Data
Sep. 26, 2018   (EP) ..................... 18306260

(51) Int. Cl.
G02C 13/00    (2006.01)
A61B 3/11     (2006.01)
H04N 23/611   (2023.01)

(52) U.S. Cl.
CPC ............ *G02C 13/005* (2013.01); *A61B 3/111* (2013.01); *H04N 23/611* (2023.01)

(58) Field of Classification Search
CPC ......... G02C 13/005; A61B 3/111; A61B 3/11; H04N 23/611
(Continued)

(56) References Cited

U.S. PATENT DOCUMENTS

2007/0035697 A1*   2/2007  Ross-Messemer .. G02C 13/005
                                                351/159.72
2008/0117384 A1    5/2008  Inakagata et al.
(Continued)

FOREIGN PATENT DOCUMENTS

WO    2015/101738    7/2015

OTHER PUBLICATIONS

Examiner provided machine translation of Baranton et al., WO 2011058244 (Year: 2011).*
(Continued)

*Primary Examiner* — Balram T Parbadia
*Assistant Examiner* — Rahman Abdur
(74) *Attorney, Agent, or Firm* — NIXON & VANDERHYE

(57) ABSTRACT

Disclosed is a method wherein the following steps are performed: a) the subject is placed in a natural posture, in which at least one of the gaze directions of the subject points to a visual target, b) an image capture apparatus is placed between the head of the subject and the visual target, c) the relative posture of the image capture apparatus and head of the subject is adjusted in order for the pupil of the image capture apparatus to be positioned close to the gaze direction of at least one of the eyes of the subject, d) an image of the head of the subject is captured, and e) the at least one geometrico-morphological parameter is deduced from this image.

20 Claims, 2 Drawing Sheets

Figure 1:
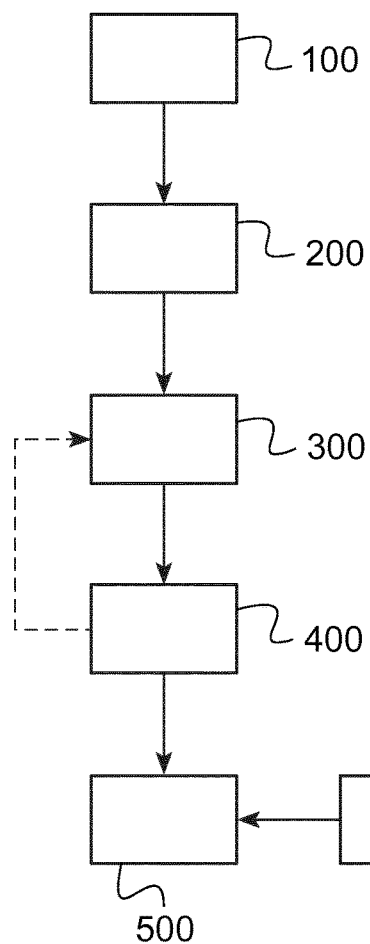

(58) Field of Classification Search
USPC .......................................................... 351/204
See application file for complete search history.

(56) References Cited

U.S. PATENT DOCUMENTS

| | | | | |
|---|---|---|---|---|
| 2011/0242481 | A1* | 10/2011 | Wada ................... | G02C 13/005 |
| | | | | 351/204 |
| 2012/0274902 | A1* | 11/2012 | Baranton ................. | A61B 3/14 |
| | | | | 351/246 |
| 2013/0215379 | A1 | 8/2013 | Sayag et al. | |
| 2015/0146168 | A1* | 5/2015 | Divo .................... | A61B 3/0091 |
| | | | | 351/204 |
| 2016/0327815 | A1* | 11/2016 | Rego .................... | G02C 13/003 |
| 2019/0028634 | A1* | 1/2019 | Koehler ................. | H04N 23/57 |

OTHER PUBLICATIONS

International Search Report for PCT/EP2019/075742 dated Nov. 25, 2019, 3 pages.
Written Opinion of the ISA for PCT/EP2019/075742 dated Nov. 25, 2019, 5 pages.
Office Action issued in European Patent Application No. 19 770 134.5 dated Aug. 21, 2023.

* cited by examiner

METHOD FOR DETERMINING AT LEAST ONE GEOMETRICO-MORPHOLOGICAL PARAMETERS OF A SUBJECT IN A NATURAL POSTURE FOR DETERMINING A VISION CORRECTION EQUIPMENT

CROSS-REFERENCE TO RELATED APPLICATIONS

This application is the U.S. national phase of International Application No. PCT/EP2019/075742 filed Sep. 24, 2019 which designated the U.S. and claims priority to EP 18306260.3 filed Sep. 26, 2018, the entire contents of each of which are hereby incorporated by reference.

TECHNICAL FIELD OF THE INVENTION

The invention relates to a method for determining at least one geometrico-morphological parameter of a subject in a natural posture for determining a vision correction equipment.

BACKGROUND INFORMATION AND PRIOR ART

Manufacturing an ophthalmic lens adapted to an individual and a frame in order to provide the individual with appropriate ophthalmic equipment requires the determination of a number of fitting data for fitting the lens in the chosen frame.

In order to obtain these fitting data, the determination of geometrico-morphological parameters of the subject is necessary.

Numerous documents describe devices and methods for determining such parameters. These parameters are for example the interpupillary distance of the subject or the fitting height, defined as the vertical distance between the pupil of the eye of the subject and the bottom edge of the frame or lens worn by the subject, in use conditions.

In order to be accurate, the measurement of the geometrico-morphological parameters of the subject such as the fitting height requires the subject to be in a natural posture.

However, it is always difficult to ensure that the subject remains in the natural posture during the image capture that will allow the determination of these parameters.

Therefore, the repeatability of known methods is not always satisfactory.

Moreover, known methods often require the use of specific instruments that are not easily available to the general public.

Finally, known methods usually require the intervention of an eye care professional. For example, the eye care professional may manually measure the fitting height with a ruler.

For these reasons, known methods do not allow precisely determining the geometrico-morphological parameters of the subject in a natural posture.

Moreover, they do not allow self determination of the parameter by the subject himself.

SUMMARY OF THE INVENTION

Therefore one object of the invention is to provide a simple method for determining at least one geometrico-morphological parameter in a reliable natural posture.

The above object is achieved according to the invention by providing a method for determining at least one geometrico-morphological parameters of a subject in a natural posture for determining a vision correction equipment, wherein the following steps are performed:

a) the subject is placed in a natural posture, in which at least one of the gaze directions of the subject points to a visual target, b) an image capture apparatus is placed between the head of the subject and said visual target, c) the relative posture of the image capture apparatus and head of the subject is adjusted in order for the pupil of the image capture apparatus to be positioned close to the gaze direction of at least one of the eyes of the subject, d) an image of the head of the subject is captured, e) the at least one geometrico-morphological parameter is deduced from this image.

Thanks to the position adjustment of step c), the eyes of the subject remains focused on the visual target. Therefore, they do not focus on the pupil of the camera. It is therefore easier for the subject to remain in the posture corresponding to a far, intermediate or near distance vision, with an eye gaze directed straight ahead of the subject, to the visual target. The posture adopted by the subject in step a) is therefore unchanged by the placement of the image capture apparatus in front of the subject. The visual target may correspond to a far distance, intermediate distance or near distance visual task.

Instructions given to the subject are simple and easy to follow, leading to a better repeatability of the method.

A further object of the invention is to provide a method that the subject is able to perform by himself. The subject is then able to perform said method by himself, with an electronic device of his own. In this way, the subject may determine the geometrico-morphological parameter by himself, at home or in any other location remote from the eye care professional's office.

Alternatively, the method according to the invention may also be implemented with dedicated tools and optional help from the eye care professional.

Advantageous and non-limiting features of the method of the invention are:

in steps c) and d), the gaze direction of at least one of the eyes of the subject points to said visual target;

in step c), the relative posture of the image capture apparatus and head of the subject is adjusted by moving the image capture apparatus without moving the head of the subject, in step d), the gaze direction of both eyes of the subject points to said pupil of the image capture apparatus and, in step e), the distance between the image capture apparatus and the eyes of the subject is taken into account for determining said parameter;

in step b), the image capture apparatus belongs to a personal electronic portable device of the subject;

in step b), the subject presses the image capture apparatus against the glass of the window and, in step c), the subject moves the image capture apparatus against the glass of the window;

the steps a) to c) are performed by the subject himself: in step a), the subject places himself in the natural posture and, in step b) and c), the image capture apparatus is manually held and moved by the subject;

the image capture apparatus comprises an inertial motion unit adapted to determine the angular position in space of the image capture apparatus, and a communication device adapted to send information on the angular position in space of the apparatus to the subject and, in step c), the image capture apparatus provides information to the subject on the angular position of the apparatus compared to a target angular position;

in step d), the image capture is triggered by the subject or automatically triggered by the image capture apparatus when the head of the subject is detected by said image capture apparatus;

the image capture apparatus is attached on a column and vertically mobile on this column;

in step e), at least one of the following parameters is determined: interpupillary distance, half interpupillary distance, fitting heights;

in step e) the dominant eye of the subject is also determined;

the image capture apparatus is positioned such that the image capture apparatus optical axis is close or parallel to the gaze direction of the subject during the capture of said image of the head of the subject;

a reference element for scaling the image is placed close to the head of the subject and, in step d), an image of the reference element is captured with the image of the head of the subject; and in step d), the subject wears no real frame and a three dimensional image of the head of the subject is captured by said image capture apparatus, in step e), a virtual frame is virtually fitted on the three dimensional image of the head of the subject and a two dimensional image of the head of the subject wearing said virtual frame is deduced, and the fitting height parameter is determined on the basis of this two dimensional image.

Preferably, in step c), the inclination of the image capture apparatus is adjusted in order for the head of the subject to be in the field of the image capture apparatus.

In an embodiment, in step d), the subject wears the chosen frame.

In another embodiment, in step e), an error of parallax is taken into account for determining said parameter.

In an embodiment, in step c), the image capture apparatus is moved by the subject or another person, either directly or indirectly.

The invention also relates to a system for determining at least one geometrico-morphological parameters of a subject in a natural posture for determining a vision correction equipment, comprising:

a visual target adapted to be placed in front of the subject, such that the subject is placed in a natural posture when at least one gaze direction of the subject points to said visual target, an image capture apparatus adapted to be placed between the head of the subject and said visual target and to capture an image of the head of the subject, adjusting means for adjusting the position and/or orientation of the image capture apparatus in order for the pupil of the image capture apparatus to be positioned close to the gaze direction of at least one of the eyes of the subject, calculating means programmed for deducing the at least one geometrico-morphological parameter from said image of the head of the subject captured with said image capture apparatus.

DETAILED DESCRIPTION OF EXAMPLE(S)

The following description, enriched with joint drawings that should be taken as non limitative examples, will help understand the invention and figure out how it can be realized.

Figure 4:
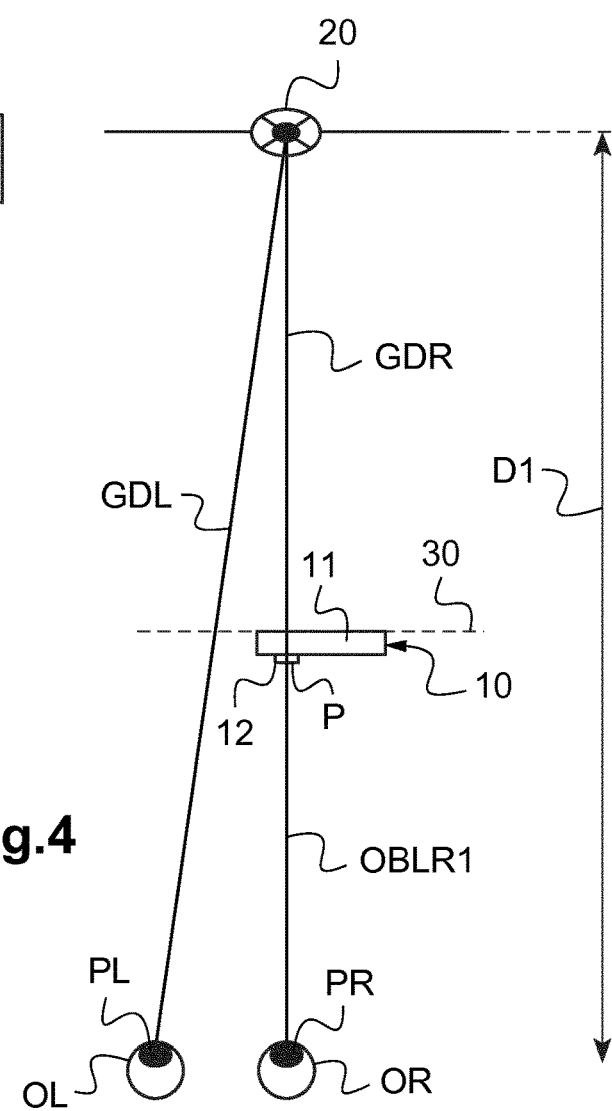
Figure 2:
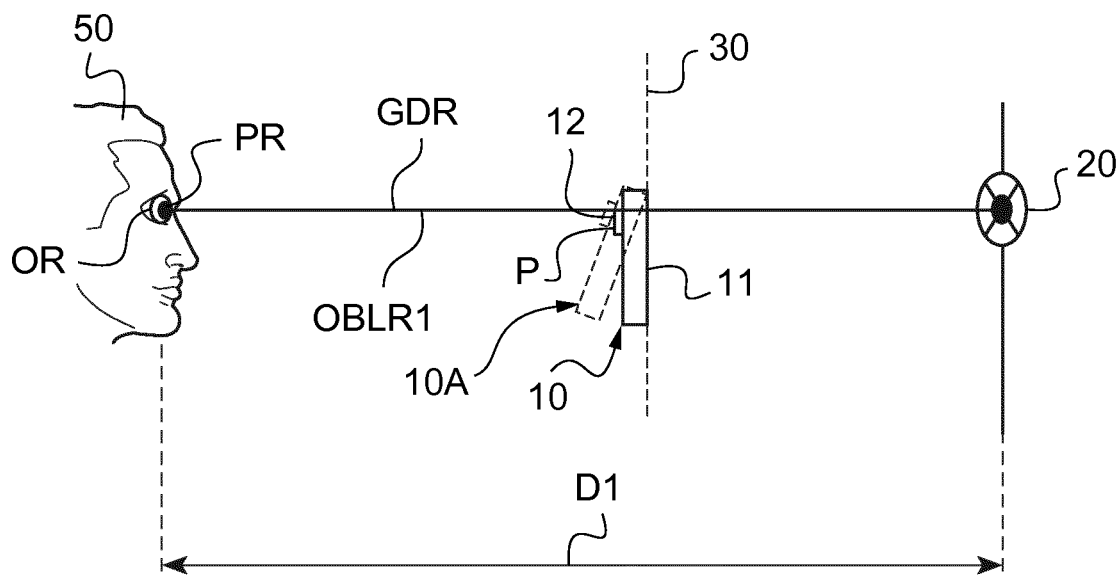
Figure 3:
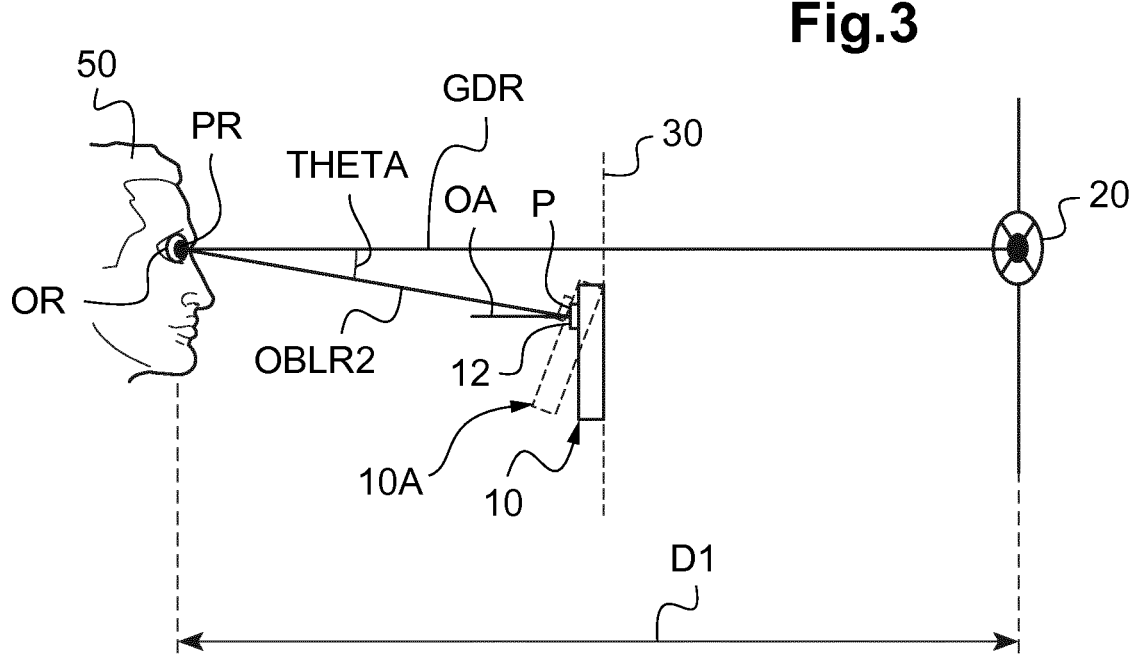

On joint drawings:

FIG. 1 is a block diagram of the steps of an embodiment of the method according to the invention, FIG. 2 is a schematic side view of a first possible relative position of the subject, electronic device and target during step d), FIG. 3 is a schematic side view of a second possible relative position of the subject, electronic device and target during step d), FIG. 4 is a schematic view from above of the first possible relative position of the subject, electronic device and target during step d).

In the following, the wording "natural posture" is defined as a posture in which the position of the head is not imposed by a physical constraint such as applying a part of the head against a surface.

According to the invention, the method for determining at least one geometrico-morphological parameters of a subject in a natural posture for determining a vision correction equipment comprises the following steps:

a) the subject is placed in a natural posture in which at least one of the gaze directions of the subject points to a visual target 20 (block 100 of FIG. 1), b) an image capture apparatus 10 is placed in front of the head 50 of the subject (block 200 of FIG. 1), c) the relative posture of the image capture apparatus 10 and head 50 of the subject is adjusted in order for the pupil P of the image capture apparatus 10 to be positioned close to the gaze direction GDL, GDR of at least one of the eyes OL, OR of the subject (block 300 of FIG. 1), d) an image of the head 50 of the subject is captured (block 400 of FIG. 1), e) the at least one geometrico-morphological parameter is deduced from this image (block 500 of FIG. 1).

In a first embodiment of the method according to the invention, the image capture apparatus 12 belongs to a portable electronic device 10 that the subject holds is his own hands.

The portable electronic device 10 is for example a smartphone or a digital tablet. It is for example a personal device of the subject. It comprises a body 11 with a screen and the image capture apparatus 12.

Instructions for performing the method may be provided to the subject via the portable electronic device. For example, the instructions maybe displayed on a screen of this device when the subject runs an application dedicated to implementing the method according to the invention.

In this case, the front camera of the smartphone, placed beside the screen is advantageously used so that the subject may read the instructions and capture the image without having to turn the smartphone.

Alternatively, it may be a portable electronic device equipped with a support allowing it to be placed in front of the head of the subject. The support is for example a stand adapted to be moved and with an adjustable height.

In a second embodiment (not shown on the figures), the image capture apparatus is attached on a column and vertically mobile. It is for example a camera or a smartphone.

In this case, instructions for performing the method may be provided to the subject via a screen placed on the column or given orally by an operator assisting the subject in performing the method.

Step a)

In step a), represented as block 100 on FIG. 1, the subject is placed in a natural posture.

Preferably, the subject places himself in the natural posture.

To this end, instructions are given to the subject to gaze at a visual target 20 placed at a specified distance D1 from his eyes (FIGS. 2 to 4).

At least one of the gaze directions GDL, GDR of the subject points to said visual target 20. Preferably, in step a), both of his gaze directions GDR, GDL points to the visual target 20.

The gaze direction GDR, GDL of each eye OR, OL of the subject is defined as the line linking the pupil of said eye to the point on which the eye is focused (FIG. 4). This gaze direction also corresponds to the line passing through the eye rotation center and the pupil center.

For example, if the geometrico-morphological parameter is to be determined in conditions of far vision, it is indicated to the subject that he should gaze at a target 20 placed as far as possible from him. This target 20 may be for example the horizon or a building placed far ahead or any target placed at a distance D1 of more than five meters. This case is shown on FIGS. 2 to 4. The figures are schematic and not to scale.

In this case, the natural posture assumed by the subject is preferably the posture where he looks straight ahead to the horizon without any constraint. This natural posture is also called orthostatic posture and corresponds to the position in which the individual achieves minimal efforts. The corresponding gaze directions are the primary gaze directions.

In this natural posture, the Frankfurt plane of the head is horizontal. The Frankfurt plane is defined as the plane passing through the inferior margin of an orbit (for example, the point called the left orbital) and the upper margin of each ear canal or external auditory meatus, a point called the porion.

In a particularly advantageous embodiment, the subject may place himself in front of a window 30 and gaze straight ahead at a distant target through the window 30. The gaze direction GDR, GDL of the subject is then the primary gaze direction and the posture of the subject is the orthostatic posture.

If the geometrico-morphological parameter is to be determined in conditions of intermediate vision, it is indicated to the subject that he should gaze at a target placed at a distance of about one meter, for example comprised between 80 centimeters and 5 meters. This target may be for example a frame on a wall or a computer screen. In this case the situation is similar to the situation shown on FIGS. 2 to 4.

If the geometrico-morphological parameter is to be determined in conditions of near vision, it is indicated to the subject that he should gaze at a target placed at a reading distance from him, for example between 25 and 50 centimeters. This target may for example comprise a text or a book placed in one of his hands or on a support, for example a table. In this case, the subject's gaze may be inclined toward the target, with a non zero angle relative to the horizontal direction. In this case, the natural posture is preferably the posture naturally assumed by the subject when reading a text (not represented on the figures).

Step b)

In step b), said image capture apparatus 12 is placed in front of the head 50 of the subject.

This image capture apparatus 12 may capture images in two or three dimensions. It may be for example the front or back camera of a smartphone or tablet, or means for acquiring three dimensional data, such as images using infra-red camera and infra-red spots projected on the head of the subject used to identify the face of the user of the smartphone.

The image capture apparatus 12 is placed between the head 50 of the subject and said visual target 20 as shown on FIGS. 2 to 4. This is verified for any distances between the head 50 and the visual target 20.

The image capture apparatus 20 may be placed in front of the head of the subject by the subject or another person.

In the first embodiment, the portable electronic device comprising the image capture apparatus is preferably placed in front of the subject by himself.

In said particularly advantageous embodiment, the subject may place the electronic portable device in front of his head 50 by placing it against said window 30. He presses the electronic portable device 10 with the image capture apparatus 12 against the glass of the window 30. For example, the subject holds the image capture apparatus at arm's length.

He is then instructed to visually superimpose the pupil P of the image capture apparatus 12 with the target 20 at step c).

In the second embodiment, the column is placed in front of the subject either by himself, by placing himself in front of the column or by another person, for example an operator assisting him by leading him to the column.

The subject may be seated or standing in front of the image capture apparatus 12.

Step c)

In step c), the relative posture of the image capture apparatus 12 and head 50 of the subject is adjusted in order for the pupil P of the image capture apparatus 12 to be positioned close to the gaze direction GDL, GDR of at least one of the eyes OL, OR of the subject.

The image capture apparatus is positioned close to the gaze direction of at least one of the eyes of the subject. Preferably, the pupil P of the image capture apparatus 12 is placed on the gaze direction GDR of one of said eyes OL, OR (FIGS. 2, 4).

Otherwise, it is preferably placed in a solid angle of about 1 to 10 degrees around the gaze direction of said at least one eye (FIG. 3).

FIG. 3 show an example where the pupil of the image capture apparatus is shifted relative to both of the gaze direction of the subject.

It is for example shifted towards the floor.

In order to perform this adjustment, the head 50 of the subject and/or the image capture apparatus 12 may be moved relative to each other.

The image capture apparatus may be moved by the subject or another person, either directly or indirectly.

The subject may move his head and/or the image capture apparatus 12 by himself.

In the first embodiment, the portable electronic device 10 is preferably moved directly by the subject who holds it in his hand. The relative posture of the image capture apparatus 12 and head 50 of the subject is adjusted by moving the image capture apparatus 12 without moving the head 50 of the subject.

In the particularly advantageous embodiment described before, the subject moves the electronic portable device 10 with the image capture apparatus 12 against the glass of the window 30. More precisely, he moves the electronic portable device 10 by translating it against the window. His head 50 remains in same position.

The subject is for example asked to move the image capture apparatus, that is to say, here, the smartphone, until the pupil P of the image capture apparatus 12 is placed right in front of one of his eyes OL, OR. The pupil P of the image capture apparatus 12 is then visually superimposed with the target 20.

Advantageously, in this situation the head of the subject will usually be entirely in the field of the image capture apparatus.

In the second embodiment, the subject may move his head 50 relative to the image capture apparatus which is attached on the column. The image capture apparatus may be moved up and/or down on the column as it is vertically mobile. The subject may move by himself and may move himself the image capture apparatus, directly or indirectly, for example manually or with a remote control or by giving instructions to another person for moving it. Alternatively, the movements of the subject and/or the image capture apparatus may be guided by another person such as the eye care professional.

Preferably, in step c), the inclination and/or position of the image capture apparatus is adjusted in order for the head of the subject to be in the field of the image capture apparatus.

Preferably, the image capture apparatus is positioned such that the image capture apparatus optical axis is close or parallel to the gaze direction of the subject during the capture of said image of the head of the subject in step d).

In the case of the first embodiment, this may be achieved manually by the subject.

Preferably, the image capture apparatus 12 is oriented such that its optical axis is parallel to the gaze axis GDL, GDR of the subject (FIGS. 2 and 3).

When the image capture apparatus 12 is part of a smartphone or tablet, the optical axis of the image capture apparatus is usually perpendicular to the screen of the device. This screen is therefore placed perpendicularly to the gaze axis of the subject. This situation is shown on FIGS. 2 to 4.

This may be easily achieved in said particularly advantageous embodiment, where the portable electronic device 10 with the image capture apparatus 12 is pressed against the glass of the window 30. The body 11 of the portable electronic device 10 that supports the screen is then applied against the glass of the window 30, meaning that the optical axis OA of the image capture apparatus 12 is mostly perpendicular to the glass of the window 30.

The subject may therefore easily look straight through the glass of the window 30, thereby having at least one of his gaze directions GDR, GDL perpendicular to the glass of the window 30 and parallel to the optical axis of the image capture apparatus 12.

In the situation of FIG. 2, where the entrance pupil P of the image capture apparatus 12 is aligned with the pupil PR of one of the eye OR of the subject, for example the right eye OR, and the target 20, the optical axis of the image capture apparatus is superposed with the gaze direction GDR of this eye OR the subject.

In this case, an observation line OBLR1 linking the pupil PR of the right eye OR of the subject and the pupil P of the image capture apparatus 12 is superposed to the gaze direction GDR of this right eye OR.

In the situation of FIG. 3, where the entrance pupil P of the image capture apparatus 12 is shifted relative to the gaze direction GDR of the subject, the optical axis OA of the image capture apparatus 12 is parallel to the gaze direction GDR of the subject.

In this case, an observation line OBLR2 linking the pupil of the right eye OR of the subject and the pupil P of the image capture apparatus 12 forms a non zero angle with the gaze direction GDR of this right eye OR.

Alternatively, especially in the case where the subject holds the image capture apparatus without applying it against a window, the optical axis of the image capture apparatus 12 may be inclined compared to the gaze axis GDR, GDL of the subject, as long as the eyes OL, OD of the subject appear on the images captured, that is to say as long as the eyes OD, OL of the subject are in the field of the image capture apparatus 12.

This situation is represented with a portable electronic device 10A in dashed lines on FIGS. 2 and 3.

In the second embodiment, the image capture apparatus may or may not be able to be inclined relative to the column. If it may be inclined, this adjustment may be performed by the subject or by the operator. Otherwise only the position adjustment is achieved.

Alternatively, the pupil of the image capture apparatus may also be placed between the eyes of the subject. It then remains close to both of the gaze directions of the subject.

In an embodiment, the image capture apparatus comprises an inertial motion unit adapted to determine the angular position in space of the device, and a communication device adapted to send information on the angular position in space of the device to the subject and, in step c), the image capture apparatus provides information to the subject on the angular position of the device compared to a target angular position.

For example, the image capture apparatus provides information to the subject on the angular position of the optical axis of the image capture apparatus compared to a horizontal axis or plane.

The information may be displayed on a screen of the electronic portable device or of the column. It may alternatively be given by a sound signal.

This is especially the case when the image capture apparatus belongs to a portable electronic device such as a smartphone or a tablet. Smartphone and tablet may be equipped with gyroscopic means able to determine their orientation in space. A target angular position may be specified and calculation means of the portable electronic device may be programmed to achieve said comparison. The inertial motion unit may also comprise an accelerometer and/or a magnetometer.

Preferably, in step c), the gaze direction GDL of the other eye OL of the subject remains pointed to said visual target 20, as shown on FIG. 4.

This means that the pupil P of the image capture apparatus 12 is placed close or on the gaze direction GDR of one of the eye OR of the subject, while the other eye OL remains focused on the visual target 20.

To this end, the size of the electronic portable device 10 is limited such that it does not obstruct the field of view of the other eye OL, OR of the subject. The other eye may therefore remain focused on the target 20 (FIG. 4).

Alternatively, the image capture apparatus 12 may be shifted upward or downward in order to allow the subject to keep both of his eyes OR, OL focused on the target 20 (FIG. 3). When the image capture apparatus 12 is shifted from the gaze directions GDR, GDL of the subject, such as in the situation shown on FIG. 3, the subject may keep both of his eyes OL,OR focused on the visual target 20 while capturing the image in step d).

Advantageously, accommodation of the eyes of the subject on the image capture apparatus is thus avoided.

This is particularly advantageous when the geometrico-morphological parameter is being determined in conditions of far vision.

Advantageously, in the case where the pupil of the image capture apparatus is placed between the eyes of the subject, the subject uses a small portable electronic device that does not obstruct the vision of the subject when it is placed between the eyes of the subject. This allows him to keep both of his eyes focused on the visual target while capturing the image in step d). This small portable electronic device is for example a smartphone and presents a typical width of about 5 to 8 centimeters.

The entrance pupil of the image capture apparatus may then be at the same level than the pupil of the eyes.

At step d), the image may be captured in natural posture, without accommodation on the image capture apparatus 12.

In the case of the intermediate and near vision measurements, accommodation is expected. However, the use of the method allows keeping the accommodation of the eye on a target placed at a predetermined distance. The measurement corresponds then precisely to the visual conditions set by the visual target.

In any case, the fact that one of the eyes remains focused on the visual target leads to the capture of an image of the eyes in the visual conditions set by the visual target, with no perturbation due to the placement of the image capture apparatus between the eyes and the target.

Alternatively, the gaze direction of both eyes of the subject may point to said entrance pupil of the image-capture apparatus and the eyes may be focused on this entrance pupil during said image capture in step d). This is taken into account in step e).

Step d)

In step d), an image of the head of the subject is captured by said image capture apparatus placed in the posture relative to the head of the subject determined in step c) of method according to the invention.

This image may be a two dimensional image or a three dimensional image of the head of the subject.

In step d), the image capture is triggered by the subject or automatically triggered by the image capture apparatus when the head of the subject is detected by said image capture apparatus.

In the first embodiment described here, the subject holds the portable electronic device 10 in his hands and may directly manually trigger the capture of the image when the image capture apparatus in positioned in front of his eyes as instructed, that is, with the pupil P of the image capture apparatus being on the gaze direction of one of his eyes or close to the gaze direction of at least one of his eyes.

In the second embodiment described here, the image capture apparatus is placed on a column. In this case, the subject preferably triggers the capture of an image with a remote control. Alternatively, another person may trigger the capture of the image, for example the eye care professional.

In all cases, the image capture apparatus may be programmed to recognize the head of the subject in the field of the image capture apparatus and automatically trigger the capture of the image when the head or more precisely, when the eyes of the subject is detected in said image. The image capture may also be triggered when an absence of movement is detected, meaning that the image capture apparatus is correctly positioned.

To this end, images are automatically captured and treated with a software or an application integrated in the image capture apparatus or the portable electronic device or the column for recognizing the head and/or the eyes of the subject. The images may also be sent and treated in another device or on a distant server comprising said software. Such software is well known from the man skilled in the art.

In step d), the subject may or may not wear the chosen frame in which the lens is to be fitted.

Advantageously, a reference element for scaling the image may be placed close to the head of the subject and, in step d), an image of this reference element may be captured with the image of the head of the subject.

This reference element is preferably an object with specific international standard dimensions, such as a credit card. It may alternatively be any object with a know dimension.

The subject may then determine this dimension and input this dimension in the portable electronic device or in the column.

If the chosen frame is worn by the subject, the dimensions of the frame, usually indicated inside one of the branches of the frame, may be used as a reference element for scaling the image.

Alternatively, no reference element is used and in step e), the image may be scaled using two reference point of the head of the subject, as described later.

Step e)

In step e), the at least one geometrico-morphological parameter is deduced from the image captured in step d).

More precisely, at least one of the following parameters is determined: interpupillary distance, half interpupillary distance, fitting heights.

In the case where, in step d), the gaze direction of both eyes of the subject points to said pupil of the image-capture apparatus during the capture of the image of the eyes of the subject, the distance between the image capture apparatus and the eyes of the subject is taken into account for determining said parameter.

In the first embodiment of the method, the portable electronic device may comprise GPS means and/or other positioning means allowing determining the position in space of the portable electronic device.

Different positioning means may be considered. For example, for a use in an eye care practitioner's office, a time-of-flight camera or a laser and a detection sensor may be added to the portable electronic device. At home, the individual may for example use a smartphone as the portable electronic device and the inertial measurement unit of the smartphone could be used as the positioning means.

This distance between the image capture apparatus and the eyes of the subject is for example determined thanks to a calibration step.

In this case, in the calibration step, the subject places the portable electronic device against his head, for example against his forehead, and records the position of his head thanks said GPS and/or positioning means. He then holds the device at the distance in which the image is captured and records this position as well. The distance between the head of the subject and the image capture apparatus may then be easily determined. Alternatively, the distance between the head of the subject and the image capture apparatus may be determined by other means, for example by placing in the field of view of the image capture apparatus a reference object with a know dimension such as a credit card or a printed target for scaling the image.

In the cases where the pupil P of the image capture apparatus 12 is not placed on the gaze direction of one of the eyes of the subject, an error of parallax may be determined so that it may be taken into account for determining said parameter.

For example, when the pupil P of the image capture apparatus is placed below the gaze direction of the subject, an error of parallax may be determined in order to determine the fitting height of the subject.

When the pupil P of the image capture apparatus is shifted laterally, that is in a horizontal plane from the gaze direction of the subject, an error of parallax may be determined in order to determine the interpupillary or half interpupillary distances.

The interpupillary distance is determined by measuring the distance between the centers of the images of the pupils of said captured image. The right and left pupillary distances are determined by measuring the distance between the centers of the images of each of the pupils and the image of the middle of the bridge of the frame.

In an embodiment where the subject wears his real chosen frame during step d) of image capture, the fitting height may be determined by measuring the distance between the center of the image pupil of the eye of the subject and the bottom edge of the image of the lens on said image captured.

It is deduced from this measure thanks to the scale factor of the image determined and, optionally, after a correction due to a parallax error.

For example, for angle theta between the gaze direction GDR of the subject and the observation line OBLR2 linking the pupil of the eye OR of the subject and the pupil P of the image capture apparatus 12, the corrected value of the fitting height $FH_{corrected}$ would be equal to the initially determined fitting height $FH_{measured}$ value based on the image captured minus the product of the distance DVO between the eye and the ophthalmic lens placed in the frame when worn by the subject (not shown on FIG. 3) and the tangent of the angle theta: $FH_{corrected}=FH_{measured}-DVO\cdot\tan(theta)$.

The distance between the eye and the lens is determined as the distance between the center of rotation of the eye and the back surface of the lens. It is estimated to be about 24 millimeters.

The angle theta is determined for example thanks to the inertial motion unit and/or thanks to a treatment of the image captured. It may also be estimated. It is typically comprised between 1 and 10 degrees.

The angle theta may be defined in the application dedicated to implementing the method according to the invention.

The individual or the eye care practitioner adjusts the position of the smartphone with help from an indicator on a live video (for example in the case of the eye care practitioner) or with help from a sonar signal for the individual.

If no image of a reference element is present on the image captured to scale the image, the image may be scaled using two reference points of the head of the subject. For example, it is possible to detect the center of the image of the pupils of the subject on said captured image and measure the interpupillary distance of the subject by another mean, for example with a pupilometer or a ruler. The image then can be scaled by using the value of the interpupillary distance thus determined and comparing it to the distance between the images of the center of the image of the pupils. Other remarkable points of the head may be used.

When the individual wears eyeglasses, the dimensions of the eyeglasses may be used. It is for example possible to use the width of the right or left circle or the width of the bridge, as noted inside one of the temples.

In another embodiment, in step d), the subject wears no real frame. In this case, a three dimensional image of the head of the subject is captured by said image capture apparatus in step d).

A virtual representation of the frame chosen by the subject is determined in an additional step (block 600 of FIG. 1). This determination may comprise retrieving a model of said chosen frame from a database, scanning the real frame with a 3D scanner in order to determine said virtual representation of the frame, or measuring some of the elements of the real frame (such as width, length of temples, bridge width . . . ).

Advantageously, when using the method according to the invention for ordering eyeglasses online, a set of frames having geometric features adapted to the head of the subject is selected from a database of frames as a function of the three dimensional image of the head of the subject captured. This database comprises the virtual representation of different frames.

The virtual representation of the chosen frame is called hereinafter the virtual frame. It comprises at least a list of geometrical feature of the chosen frame, such as temple length, width of the bridge, width of the circles, wrap angle, total width.

The step of selecting the appropriate frame may be done by virtually fitted the virtual frame of the three dimensional image of the subject head, as is known for example from document WO2015101738.

In a further step, the selected frames are submitted to the subject and the subject chooses the frame he would like to purchase among this selection.

In step e), said virtual frame is virtually fitted on the three dimensional image of the head of the subject and a two dimensional image of the head of the subject wearing said virtual frame is deduced.

By virtually fitted, it is meant that the virtual frame is overlaid on the three dimensional image of the head in order to be placed on the head as it would be placed when worn by the subject. To this end, methods of virtual fitting are well known where remarkable part of the virtual frame are superimposed on remarkable zones of the three dimensional image of the head.

Once the virtual frame is virtually fitted to the three dimensional image of the head of the subject, a projection of the three dimensional representation thus obtained is determined in a frontal plane. The frontal plane is perpendicular to the sagittal plane of the head of the subject and to the Frankfurt plane of the head of the subject.

This projection forms a two dimensional image of the head equipped with the virtual frame.

The fitting height of the subject equipped with the chosen frame is determined on the basis of the two dimensional image thus determined, as described before. The right and left pupillary distances may also be determined based on the two dimensional image as the distance between the center of the pupil of each eye and the middle of the bridge of the frame.

In the case where the subject is instructed to place the pupil of the image capture apparatus on the gaze direction of one of his eyes, that is, to superimpose the pupil of the image capture apparatus with the target, without specifying on the gaze direction of which eye it should be placed, the dominant eye of the subject may also be determined as the eye corresponding to the gaze direction on which the subject places the pupil of the image capture apparatus. The image of the dominant eye is indeed positioned in the center of the captured image.

The invention claimed is:

1. A method for determining at least one geometrico-morphological parameter of a subject in a natural posture to determine a vision correction equipment, the method comprising the following steps:
   a) placing the subject in a natural posture, in which at least one of the gaze directions of the subject points to a visual target;

b) placing an image capture apparatus between the head of the subject and said visual target on a line linking one of the eyes of the subject and the visual target, the image capture apparatus including a pupil;

c) adjusting the relative posture of the image capture apparatus and the head of the subject in order for the pupil of the image capture apparatus to be positioned close to the gaze direction of at least one of the eyes of the subject;

d) capturing an image of the head of the subject; and e) deducing the at least one geometrico-morphological parameter from the captured image.

2. The method according to claim 1, wherein, in steps c) and d), the gaze direction of at least one of the eyes of the subject points to said visual target.

3. The method according to claim 2, wherein:

in step c), the relative posture of the image capture apparatus and the head of the subject is adjusted by moving the image capture apparatus without moving the head of the subject, and in step d), the gaze direction of both of the eyes of the subject points to said pupil of the image capture apparatus, and in step e), the distance between the image capture apparatus and the eyes of the subject is taken into account to determine said at least one geometrico-morphological parameter.

4. The method according to claim 2, wherein, in step b), the image capture apparatus belongs to a personal electronic portable device of the subject.

5. The method according to claim 2, wherein, in step a), the subject looks into the distance through a window, in step b), the subject presses the image capture apparatus against glass of the window, and in step c), the subject moves the image capture apparatus against the glass of the window.

6. The method according to claim 1, wherein:

in step c), the relative posture of the image capture apparatus and the head of the subject is adjusted by moving the image capture apparatus without moving the head of the subject, and in step d), the gaze direction of both of the eyes of the subject points to said pupil of the image capture apparatus, and in step e), the distance between the image capture apparatus and the eyes of the subject is taken into account to determine said at least one geometrico-morphological parameter.

7. The method according to claim 6, wherein, in step b), the image capture apparatus belongs to a personal electronic portable device of the subject.

8. The method according to claim 6, wherein, in step a), the subject looks into the distance through a window, in step b), the subject presses the image capture apparatus against glass of the window, and in step c), the subject moves the image capture apparatus against the glass of the window.

9. The method according to claim 1, wherein, in step b), the image capture apparatus belongs to a personal electronic portable device of the subject.

10. The method according to claim 1, wherein, in step a), the subject looks into the distance through a window, in step b), the subject presses the image capture apparatus against glass of the window, and in step c), the subject moves the image capture apparatus against the glass of the window.

11. The method according to claim 1, wherein the steps a) to c) are performed by the subject himself:

in step a), the subject places himself in the natural posture, and in steps b) and c), the image capture apparatus is manually held and moved by the subject.

12. The method according to claim 1, wherein the image capture apparatus comprises an inertial motion device configured to determine the angular position in space of the image capture apparatus, and a communication device configured to send information on the angular position in space of the apparatus to the subject, and in step c), the image capture apparatus provides the information to the subject on the angular position of the apparatus compared to a target angular position.

13. The method according to claim 1, wherein, in step d), the image capture is triggered by the subject or automatically triggered by the image capture apparatus when the head of the subject is detected by said image capture apparatus.

14. The method according to claim 1, wherein the image capture apparatus is attached on a column and vertically mobile on the column.

15. The method according to claim 1, wherein, in step e), at least one of the following parameters is determined: interpupillary distance, half interpupillary distance, and fitting heights.

16. The method according to claim 1, wherein, in step e), the dominant eye of the subject is determined.

17. The method according to claim 1, wherein the image capture apparatus is positioned such that the optical axis of the image capture apparatus is close or parallel to the gaze direction of the subject during the capture of said image of the head of the subject.

18. The method according to claim 1, wherein a reference element configured to scale the image is placed close to the head of the subject, and in step d), an image of the reference element is captured with the image of the head of the subject.

19. The method according to claim 1, wherein, in step d), the subject wears no real frame and a three-dimensional image of the head of the subject is captured by said image capture apparatus, in step e), a virtual frame is virtually fitted on the three-dimensional image of the head of the subject and a two-dimensional image of the head of the subject wearing said virtual frame is deduced, the at least one geometrico-morphological parameter is a fitting height parameter determined based on the two-dimensional image.

20. A system for determining at least one geometrico-morphological parameter of a subject in a natural posture to determine a vision correction equipment, the system comprising:

a visual target configured to be placed in front of the subject, such that the subject is placed in a natural posture when at least one gaze direction of the subject points to said visual target;

an image capture apparatus configured to be placed between the head of the subject and said visual target, on a line linking one of the eyes of the subject and the visual target, the image capture apparatus being configured to capture an image of the head of the subject, the image capture apparatus including a pupil;

an adjustment system configured to adjust one or more of a position and an orientation of the image capture apparatus in order for the pupil of the image capture apparatus to be positioned close to the gaze direction of at least one of the eyes of the subject; and a calculator configured to deduce the at least one geometrico-morphological parameter from said image of the head of the subject captured with said image capture apparatus.

\* \* \* \* \*